(12) United States Patent
Karube et al.

(10) Patent No.: US 9,487,459 B2
(45) Date of Patent: *Nov. 8, 2016

(54) METHOD FOR PRODUCING FLUORINE-CONTAINING OLEFIN

(71) Applicant: DAIKIN INDUSTRIES, LTD., Osaka (JP)

(72) Inventors: Daisuke Karube, Osaka (JP); Tatsuya Takakuwa, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/778,631

(22) PCT Filed: Mar. 7, 2014

(86) PCT No.: PCT/JP2014/055971
§ 371 (c)(1),
(2) Date: Sep. 21, 2015

(87) PCT Pub. No.: WO2014/174918
PCT Pub. Date: Oct. 30, 2014

(65) Prior Publication Data
US 2016/0052841 A1   Feb. 25, 2016

(30) Foreign Application Priority Data

Apr. 25, 2013  (JP) .................................. 2013-092122

(51) Int. Cl.
  C07C 17/00    (2006.01)
  C07C 17/20    (2006.01)
(52) U.S. Cl.
  CPC ............. *C07C 17/20* (2013.01); *C07C 17/206* (2013.01)
(58) Field of Classification Search
  CPC ... C07C 17/206; C07C 17/205; C07C 21/18; C07C 17/10; C07C 17/25
  USPC ........................................ 570/155, 165, 169
  See application file for complete search history.

(56) References Cited

U.S. PATENT DOCUMENTS

| | | | |
|---|---|---|---|
| 4,465,786 A | | 8/1984 | Zimmer et al. |
| 5,811,603 A | * | 9/1998 | Elsheikh ................. C07C 17/00 570/166 |
| 2005/0222472 A1 | | 10/2005 | Merkel et al. |
| 2007/0027348 A1 | | 2/2007 | Quan et al. |
| 2009/0105510 A1 | | 4/2009 | Quan et al. |
| 2010/0168482 A1 | | 7/2010 | Rao et al. |
| 2011/0130599 A1 | * | 6/2011 | Elsheikh ................ C07C 17/206 570/160 |
| 2011/0155942 A1 | * | 6/2011 | Pigamo ................. B01J 23/866 252/2 |
| 2011/0160497 A1 | | 6/2011 | Deur-Bert et al. |
| 2013/0035526 A1 | | 2/2013 | Elsheikh et al. |
| 2013/0060068 A1 | | 3/2013 | Rao et al. |
| 2013/0217928 A1 | | 8/2013 | Takahashi et al. |

FOREIGN PATENT DOCUMENTS

| | | |
|---|---|---|
| CN | 1218789 | 6/1999 |
| CN | 102686543 | 9/2012 |
| JP | 59-80332 | 5/1984 |
| JP | 2007-38216 | 2/2007 |
| JP | 2007-531732 | 11/2007 |
| WO | 2008/054782 | 5/2008 |
| WO | 2011/077394 | 6/2011 |
| WO | 2011/130108 | 10/2011 |
| WO | 2012/057367 | 5/2012 |

OTHER PUBLICATIONS

International Search Report issued May 20, 2014 International Application No. PCT/JP2014/055971.

* cited by examiner

*Primary Examiner* — Jafar Parsa
(74) *Attorney, Agent, or Firm* — Wenderoth, Lind & Ponack, L.L.P.

(57) ABSTRACT

The present invention provides a method for producing a fluorine-containing olefin, the method comprising reacting a chlorine-containing compound represented by a specific formula with anhydrous hydrogen fluoride in the presence of a chromium atom-containing fluorination catalyst, the reaction being carried out at a temperature within the range of 200 to 350° C. in the presence of 0.0001 to 0.03 mol of molecular chlorine per mol of the chlorine-containing compound. The present invention is capable of achieving the effect of suppressing catalyst deterioration, maintaining the starting material conversion and the target product selectivity within excellent ranges, and reducing adverse effects caused by the use of a large amount of non-condensable gas.

7 Claims, No Drawings

METHOD FOR PRODUCING FLUORINE-CONTAINING OLEFIN

TECHNICAL FIELD

The present invention relates to a method for producing a fluorine-containing olefin.

BACKGROUND ART

Fluoroolefins represented by formula: $CF_3(CX_2)_nCF=CH_2$, formula: $CF_3(CX_2)_nCH=CHF$, and the like are compounds having a useful structure as various functional materials, solvents, refrigerants, blowing agents, and the monomers for functional polymers or the starting materials of such monomers. Fluoroolefins are used, for example, as monomers for modifying an ethylene-tetrafluoroethylene copolymer. Of these fluoroolefins, the compound represented by $CF_3CH=CH_3$ (HFO-1234yf) and the compound represented by $CF_3CH=CHF$ (HFO-1234ze) have recently gained attention, as they offer promising prospects as refrigerants with low global warming potential.

As an example of methods for producing the fluoroolefins represented by the formulae above, a method has been reported in which a chlorine-containing alkane or chlorine containing alkene starting material having the same number of carbon atoms as that of a target fluoroolefin is reacted with a fluorinating agent, such as an anhydrous hydrogen fluoride, in the presence of a catalyst (see Patent Literature (PTL) 1 below).

In particular, HFO-1234yf, which is gathering attention as a refrigerant with low global warming potential, is produced by a gas-phase continuous fluorination reaction of chlorine-containing olefins, such as HCFO-1233xf, in the presence of a catalyst. A method is also known that additionally uses a gas having oxidizing properties, such as oxygen and chlorine, to prevent catalyst deterioration caused by a long-term continuous reaction.

However, the use of oxygen gas to prevent catalyst deterioration requires a reaction temperature of about 350° C. or higher. If the reaction is performed at a temperature of about 350° C. or lower so as to maintain optimum selectivity or optimum catalyst stability, it is impossible to sufficiently obtain an effect of suppressing catalyst deterioration. Furthermore, to sufficiently obtain an effect of suppressing catalyst deterioration, a relatively large amount of oxygen is required.

The addition of chlorine gas to prevent catalyst deterioration poses a problem in that chlorine gas, which has a high reactivity, acts on the starting material or product, and reduces the selectivity of the target product. In particular, the thermal addition of chlorine gas easily occurs with respect, to a double-bond-containing starting material or product, which results in a great reduction in the selectivity of the target product.

Moreover, in any case, when a gas for preventing deterioration is once added, it stays with the fluoroolefin until the end of the production process, causing a problem at the time of purification in that the gas serves as a non-condensable gas and inhibits the separation and purification of fluoroolefin.

CITATION LIST

Patent Literature

PTL 1: US20110160497

SUMMARY OF INVENTION

Technical Problem

The present invention has been, accomplished in view of the foregoing state of the art, and the primary object of the present invention is to provide a method for producing a fluorine-containing olefin by reacting a chlorine-containing alkane or chlorine-containing alkene starting material with anhydrous hydrogen fluoride in the presence of a catalyst, the method being capable of sufficiently achieving an effect of suppressing catalyst deterioration, maintaining the starting material conversion and the target product selectivity within excellent ranges, and reducing adverse effects caused by the use of a large amount of non-condensable gas.

Solution to Problem

The present inventors conducted extensive research to achieve the above object and found the following. Specifically, in a method comprising reacting a specific chlorine-containing alkane or chlorine-containing alkene used as a starting material with anhydrous hydrogen fluoride in the presence of a catalyst, when a small amount of molecular chlorine (less than 3 mol %) is added as a catalyst deterioration inhibitor to the starting compound, and the reaction is performed at a temperature as relatively low as 200 to 350° C., an effect of suppressing catalyst deterioration is sufficiently achieved while the starting material conversion and the target product selectivity are maintained within excellent ranges. Such a small amount of chlorine added as a catalyst deterioration inhibitor only slightly inhibits the separation and purification of the target product, and thus enables efficient production of a fluorine-containing olefin. The present invention has thereby been accomplished.

More specifically, the present invention provides the following method for producing a fluorine-containing olefin.

Item 1. A method for producing a fluorine-containing olefin represented by Formula (7); $CF_3CA=CHB$, wherein one of A or B is F, and the other is H, the method comprising reacting anhydrous hydrogen fluoride with at least one chlorine-containing compound in the presence of a chromium atom-containing fluorination catalyst, the at least one chlorine-containing compound being selected from the group consisting of a chlorine-containing alkane represented by Formula (1); $CX_3CClYCH_2Z$, wherein X is independently F or Cl, Y is H or F, when Y is H, Z is Cl or F, and when Y is F, Z is H;

a chlorine-containing alkane represented by Formula (2): $CX_3CH_2CHX_2$, wherein X is independently F or Cl, and at least one X is Cl;

a chlorine-containing alkene represented by Formula (3): $CX_3CCl=CH_2$, wherein X is independently F or Cl;

a chlorine-containing alkene represented by Formula (4): $CX_3CH=CHX$, wherein X is independently F or Cl, and at least one X is Cl;

a chlorine-containing alkene represented by Formula (5): $CH_2XCCl=CX_2$, wherein X is independently F or Cl; and a chlorine-containing alkene represented by Formula (6): $CHX_2CH=CX_2$, wherein X is independently F or Cl, and at least one X is Cl;

the reaction being carried out at a temperature within a range of 200 to 350° C. in the presence of 0.0001 to 0.03 mol of molecular chlorine per mol of the chlorine-containing compound.

Item 2. The method for producing a fluorine-containing olefin according to Item 1, wherein the chlorine-containing compound is at least one compound selected, from the group consisting of 2,3-dichloro-1,1,1-trifluoropropane, 1,2,3-trichloro-1,1-difluoropropane, 1,1,2,3-tetrachloro-1-fluoropropane, 1,1,1,3,3-pentachloropropane, 2-chloro-3,3,3-trifluoropropene, 2,3,3,3-tetrachloropropene, 2,3-dichloro-3,3-difluoropropene, 1-chloro-3,3,3-trifluoropropene, 1,3,3,3-tetrachloropropene, 1,1,2,3-tetrachloropropene, and 1,1,3,3-tetrachloropropene.

Item 3. The method for producing a fluorine-containing olefin according to Item 1 or 2, wherein the chlorine-containing compound is 2-chloro-3,3,3-trifluoropropene, and the reaction temperature is 300 to 350° C.

Item 4. The method for producing a fluorine-containing olefin according to any one of Items 1 to 3, wherein the molecular chlorine is used in an amount of 0.001 to 0.01 mol per mol of the chlorine-containing compound.

The method for producing a fluorine-containing olefin of the present invention is specifically described below.

(I) Starting Compound

As a starting material, the present invention uses at least one chlorine-containing compound selected from the group consisting of the compounds represented by Formulae (1) to (6) below.

A chlorine-containing alkane represented by Formula (1); $CX_3CClYCH_2Z$, wherein X is independently F or Cl, Y is H or F, when Y is H, Z is Cl or F, and when Y is F, Z is H;

a chlorine-containing alkane represented by Formula (2); $CX_3CH_2CHX_2$, wherein X is independently F or Cl, and at least one X is Cl;

a chlorine-containing alkene represented by Formula (3): $CX_3CCl=CH_2$, where in X is independently F or Cl;

a chlorine-containing alkene represented by Formula (4); $CX_3CH=CHX$, wherein X is independently F or Cl, and at least one X is Cl;

a chlorine-containing alkene represented by Formula (5); $CH_3XCCl=CX_2$, wherein X is independently F or Cl; and a chlorine-containing alkene represented by Formula (6); $CHX_2CH=CX_2$; wherein X is independently F or Cl.

When these chlorine-containing compounds are used as a starting material, and reacted with anhydrous hydrogen fluoride under the conditions described later, a target fluorine-containing olefin represented by Formula (7): $CF_3CA=CHB$, wherein one of A or B is F, and the other is H, is obtained with high selectivity.

Of the starting compounds mentioned above, specific examples of chlorine-containing alkanes represented by Formula (1): $CX_3CClYCH_2Z$ include 2,3-dichloro-1,1,1-trifluoropropane ($CF_3CHClCH_2Cl$ (HCFC-243db)), 1,2,3-trichloro-1,1-difluoropropane ($CF_2ClCHClCH_2Cl$ (HCFC-242dc)), 1,1,2,3-tetrachloro-1-fluoropropane ($CFCl_2CHClCH_2Cl$ (HCFC-241dc)), and the like. Specific examples of chlorine-containing alkanes represented by Formula (2): $CX_3CH_2CHX_2$ include 1,1,1,3,3-pentachloropropane ($CCl_3CH_2CHCl_2$ (HCC-240fa)) and the like. Specific examples of chlorine-containing alkenes represented by Formula (3): $CX_3CCl=CH_2$ include 2-chloro-3,3,3-trifluoropropene ($CF_3CCl=CH_2$ (HCFC-1233xf)), 2,3,3,3-tetrachloropropene ($CCl_3CCl=CH_2$ (HCO-1230xf)), 2,3-dichloro-3,3-difluoropropene ($CF_2ClCCl=CH_2$ (HCFO-1232xf)), and the like. Specific examples of chlorine-containing alkenes represented by Formula (4): $CX_3CH=CHX$ include 1-chloro-3,3,3-trifluoropropene ($CF_3CH=CHCl$ (HCFO-1233zd)), 1,3,3,3-tetrachloropropene ($CCl_3CH=CHCl$ (HCO-1230zd)), and the like. Specific examples of chlorine-containing alkenes represented by Formula (5) $CH_2XCCl=CX_2$ include 1,1,2,3-tetrachloropropene ($CH_2ClCCl=CCl_2$ (HCO-1230xa)). Specific examples of chlorine-containing alkenes represented, by Formula (6): $CHX_2CH=CX_2$ include 1,1,3,3-tetrachloropropene ($CHCl_2CH=CCl_2$ (HCO-1230za)) and the like.

In the present invention, the starting compounds above may be used alone or in a combination of two or more.

(II) Reaction Process

In the production method of the present invention, the starting compound mentioned above is reacted with hydrogen fluoride in the presence of a chromium atom-containing catalyst. In this method, when the reaction is carried out at a temperature within a range of 200 to 350° C. in the presence of 0.0001 to 0.03 mol of molecular chlorine per mol of the starting compound, an effect of suppressing catalyst deterioration is sufficiently achieved regardless of the small amount of chlorine used, and it is also possible to maintain the starting material conversion and the selectivity of the target fluorine-containing olefin within excellent ranges.

The amount of molecular chlorine supplied must be adjusted to about 0.0001 to 0.03 mol, and preferably about 0.001 to 0.01 mol, per mol of a chlorine-containing compound used as the starting material. In the present invention, the reaction temperature is adjusted within the range described later, in this manner, an effect in which catalyst deterioration is suppressed is sufficiently achieved by using such a relatively small amount of molecular chlorine, and excellent selectivity is also maintained.

The method of performing the reaction in the presence of molecular chlorine is not particularly limited. In general, molecular chlorine may be supplied to a reactor together with a chlorine-containing compound used as the starting material. Molecular chlorine may also be supplied to a reactor after being dissolved in a chlorine-containing compound.

In the production method of the present invention, a chromium atom-containing fluorination catalyst is used as a catalyst. Examples of usable chromium atom-containing fluorination catalysts include halides, oxides, and the like. Of these, examples of preferable catalysts include $CrCl_3$, $CrF_3$, $Cr_2O_3$, $CrO_2$, $CrO_3$, and the like. These catalysts may be supported on a carrier. Examples of carriers include, but are not particularly limited to, porous alumina silicates typified by zeolites, aluminum oxides, silicon oxides, activated carbons, titanium oxides, zirconia oxides, zinc oxides, aluminum fluorides, and the like.

In the present invention, it is particularly preferable to use at least one catalyst selected from the group consisting of chromium oxides and fluorinated chromium oxides. Examples of usable chromium oxide catalysts and fluorinated chromium oxides include crystalline chromium oxides, amorphous chromium oxides, and the like.

There is no particular limitation on the composition of chromium oxides. For example, it is preferable to use chromium oxides represented by the composition formula: $CrO_m$, wherein m is in the range of $1.5<m<3$, and more preferably $2<m<2.75$.

Usable chromium oxide catalysts may be in any form, such as powder form or pellet form as long as they are suitable for the reaction. Of these, chromium, oxide catalysts in pellet form, are preferable. The above-mentioned chromium oxide catalysts can be produced, for example, by the method disclosed in JPH05-146680A.

Fluorinated chromium oxides may be prepared, for example, by fluorinating chromium oxides obtained by the above-described method with hydrogen fluoride (HF treatment). The fluorination temperature may be, for example, about 100 to 460° C. For example, fluorination of chromium oxide may be carried out by supplying anhydrous hydrogen fluoride to a reactor containing chromium oxide. After chromium oxide is fluorinated in this manner, the starting material is supplied to the reactor, thereby allowing the reaction for producing a desired product to proceed efficiently.

In the method of the present invention, the reaction is carried out in the presence of hydrogen fluoride. This is probably the reason why the fluoridation of the catalyst proceeds during the reaction even when a fluorination treatment is not performed in advance.

The degree of fluorination is not particularly limited. For example, a chromium oxide having a fluorine content of about 5 to 30 wt % may be suitably used.

The surface area of the catalyst is varied as a result of the fluorination treatment. In general, the greater the specific surface area, the higher the activity. The specific surface area of chromium oxide after fluorination is preferably about 25 to 130 m$^2$/g, but is not limited to this range.

Further, a catalyst disclosed in JPH11-171806A, which comprises, as a main component, a chromium compound containing at least one metal element selected from the group consisting of indium, gallium, cobalt, nickel, sine, and aluminum, may also be used as a chromium oxide catalyst or a fluorinated chromium oxide catalyst.

There is no particular limitation on the method of using the catalyst as long as the catalyst is used in such a manner that the starting material is sufficiently brought into contact with the catalyst. For example, a method of forming a catalyst layer by immobilizing a catalyst in a reactor, a method of dispersing a catalyst in a fluidized bed, or other methods may be employed.

Anhydrous hydrogen fluoride may be generally supplied to a reactor together with the starting compound. The amount of anhydrous hydrogen fluoride to foe used is not particularly limited. To achieve high selectivity of the target fluorine-containing olefin, the amount of anhydrous hydrogen fluoride is preferably about 4 mol or more, and more preferably 8 mol or more, per mol of a chlorine-containing compound used as the starting material.

The upper limit of the amount of anhydrous hydrogen fluoride is not particularly limited. Even if the amount of hydrogen fluoride is excessively large, little influence is exerted on the selectivity and conversion; however, the productivity decreases because of an increase in the amount of hydrogen fluoride separated during purification. For this reason, the amount of anhydrous hydrogen fluoride is generally preferably about 100 mol or less, and more preferably about 50 mol or less, per mol of a chlorine-containing compound used as the starting material.

In the present invention, the reaction temperature must be within the range of 200 to 350° C. When the reaction is performed in such a relatively low-temperature range in the presence of molecular chlorine in the specific amount described above, an effect in which catalyst deterioration is suppressed is sufficiently achieved while high selectivity of the target fluorine-containing olefin is obtained with reduced formation of by-products, and the starting material conversion is also maintained within an excellent range.

In the method of the present invention, a preferable reaction temperature may be selected within the temperature range mentioned above, depending on the starting compound to be used. For example, when 2-chloro-3,3,3-trifluoropropene (HCFO-1233xf) is used as the starting material, the reaction temperature is preferably about 300 to 350° C., and more preferably about 325 to 350° C., to obtain the starting material conversion and target product selectivity within excellent ranges. In this case, in particular, the amount of molecular chlorine used is preferably about 0.001 to 0.03 mol, and more preferably about 0.001 to 0.01 mol, per mol of 2-chloro-3,3,3-trifluoropropane (HCFO-1233xf).

The pressure during the reaction is not particularly limited, and the reaction may be conducted under reduced pressure, ordinary pressure, or increased pressure. Although the reaction may be generally carried out at a pressure near atmospheric pressure (0.1 MPa), it can also proceed smoothly under reduced pressure of less than 0.1 MPa. The reaction may also be conducted under increased pressure within a range in which the starting material does not liquefy.

Examples of specific embodiments of the method of the present invention include a method comprising placing a fluorination catalyst into a tubular flow reactor, and introducing a chlorine-containing compound used as the starting material, anhydrous hydrogen fluoride, and molecular chlorine into the reactor.

The starting compound may be in a liquid form when supplied as long as the starting compound is in a gaseous form when it comes into contact with anhydrous hydrogen fluoride. For example, when the starting compound is liquid at an ordinary temperature and ordinary pressure, the starting compound is vaporized using a vaporizer (vaporization region), passed through a preheating region, and then supplied to a mixing region in which the starting compound is brought, into contact with anhydrous hydrogen fluoride. In this manner, the reaction is conducted in a gas phase. The reaction may also be carried out by supplying the starting compound in a liquid form to a reaction apparatus, heating a catalyst layer placed in the reactor to the vaporization temperature of the starting compound or higher, and vaporizing the starting compound when the compound enters a reaction region to react with hydrogen fluoride.

The reactor is preferably made of a material resistant to the corrosive action of hydrogen fluoride, such as Hastelloy, Inconel, Monel, or the like.

The starting material mentioned above may be directly supplied to the reactor. If dilution is required to control the reactivity, the starting material may be supplied together with nitrogen, helium, argon, or another gas that is inert to the starting material and catalyst. It is also possible to use oxygen gas together.

When inert gas and/or oxygen gas is added, the amount thereof is desirably within a range that does not cause an unnecessary reduction in reactivity due to dilution, or within a range that does not reduce the purification efficiency as a non-condensable gas in a subsequent step. The concentration is preferably such that the total amount of the inert gas and oxygen gas is about 10 mol % or less, based on the total amount of the gas components introduced into the reactor, i.e., the chlorine-containing compound, anhydrous hydrogen fluoride, and chlorine gas, in addition to inert gas and oxygen gas.

Although the contact time is not limited, an excessively short contact time can result in insufficient conversion in the reaction while an excessively long contact time can result in an increased formation of undesirable by-products. Bearing this in mind, an appropriate contact time may be selected. For example, the contact time, which is represented by $W/F_0$, is preferably adjusted to about 0.5 to 70 g·see/mL, and more preferably about 1 to 50 g·sec/mL. $W/F_0$ is the ratio of the amount of catalyst used $W(g)$ to the total flow rate $F_0$ (flow rate at 0° C., 0.1 MPa: mL/sec) of the starting material gas supplied to the reaction system. The total flow of the starting material gas as used herein refers to the total of the flow of the chlorine-containing compound, anhydrous hydrogen fluoride, and chlorine, and, when used, the flow of inert gas, oxygen gas, and the like.

(III) Reaction Product

The method described above is capable of producing a target fluorine-containing olefin represented by Formula (7): $CF_3CA\!=\!CHB$, wherein one of A or B is F, and the other is H, with high selectivity by using a chlorine-containing compound represented by Formulae (1) to (6) as the starting material. Even when the reaction is continued, a decrease in the catalytic activity is prevented, and high selectivity is maintained for a long period of time.

Specific examples of fluorine-containing olefins represented by Formula (7) include 2,3,3,3-tetrafluoropropene (HFO-1234yf) represented by formula: $CF_3CF\!=\!CH_2$, 1,3,3,3-tetrafluoropropene (HFO-1234ze) represented by formula: $CF_3CH\!=\!CHF$, and the like. For example, the use of $CF_3CHClCH_2Cl$ (HCFC-243db), $CF_2ClCHClCH_2Cl$ (HCFC-242dc), $CFCl_2CHClCH_2Cl$ (HCFC-241dc), $CF_3CCl\!=\!CH_2$ (HCFO-1233xf), $CF_3ClCCl\!=\!CH_2$ (HCFO-1232xf), $CH_2ClCCl\!=\!CCl_2$ (HCO-1230xa), $CCl_3CCl\!=\!CH_2$ (HCO-1230xf), or the like as the starting material yields 2,3,3,3-tetrafluoropropene (HFO-1234yf) as a main component. The use of $CCl_3CH_2CHCl_2$ (HCC-240fa), $CHCl_2CH\!=\!CCl_2$ (HCO-1230za), $CF_3CH\!=\!CHCl$ (HCFO-1233zd), $CCl_3CH\!=\!CHCl$ (HCO-1230zd), or the like as the starting material yields 1,3,3,3-tetrafluoropropene (HFO-1234ze) as a main component.

In the method of the present invention, a target fluorine-containing olefin represented by Formula (7) is obtained after the product obtained at the reactor outlet is separated and collected by distillation or the like.

1,1,1,2,2-Pentafluoropropane (HFC-245cb), a main component of by-products contained in the product, can be easily converted into 2,3,3,3-tetrafluoropropene (HFO-1234yf) by dehydrofluorination reaction, and can be effectively used as a useful compound.

Advantageous Effects of Invention

The method of the present invention, which uses a chlorine-containing compound represented by a specific formula as a starting material, is capable of producing a target fluorine-containing olefin with high selectivity in a moderate starting material conversion. Even when the reaction is continued, a decrease in catalytic activity is prevented, and high selectivity is maintained for a long period of time.

Further, in the method of the present invention, a relatively small amount of molecular chlorine is used as a catalyst deterioration inhibitor, making it easy to separate and purify the target product from the obtained product.

As described above, the method of the present invention is capable of continuously and efficiently producing a fluorine-containing olefin in a high yield without requiring complicated treatments, such as catalyst replacement and catalyst regeneration treatment, for a long period of time.

Therefore, the method of the present invention is industrially very advantageous as a method for producing a fluorine-containing olefin.

DESCRIPTION OF EMBODIMENTS

Hereinafter, the present invention is described in more detail with reference to Examples.

Example 1

A chromium oxide (7.0 g) represented by the composition formula: $CrO_2$ is placed in a tubular Hastelloy reactor with an inner diameter of 1.27 mm and a length of 1 m. The reactor is heated, and nitrogen gas and hydrogen fluoride gas are introduced to fluorinate the catalyst.

Subsequently, the temperature of the reactor was raised to 350° C., and hydrogen fluoride gas and chlorine gas were supplied to the reactor at flow rates of 239 Nml/min and 0.0797 Nml/min, respectively, and maintained for 0.5 hour. Thereafter, the gas of 2-chloro-3,3,3-trifluoropropene ($CF_3CCl\!=\!CH_2$ (HCFO-1233xf)) was supplied to the reactor at a flow rate of 7.97 Nml/min. About 24 hours later, the first sampling of the effluent gas from the reactor was performed, and analyzed by gas chromatography.

Table 1 shows the results. 1,1,1,2,2-Pentafluoropropane (HFC-245cb) in the product is a useful compound that can be converted into 2,3,3,3-tetrafluoropropene (HFO-1234yf) by dehydrofluorination reaction; thus, the total selectivity of HFO-1234yf and HFC-245cb is also shown in Table 1 as a total value of selectivity of useful compounds.

After the first sampling, the effluent gas from the reactor was sampled every several hours and analyzed by gas chromatography. In this manner, changes in the conversion of 1233xf were observed. Based on this conversion change data, the speed of decrease in conversion per day was calculated, which is shown in Table 1 as a measure of catalyst deterioration.

The symbols shown in the table represent the following compounds.

1233xf: 2-chloro-3,3,3-trifluoropropene
1234yf: 2,3,3,3-tetrafluoropropene
245cb: 1,1,1,2,2-pentafluoropropane
1223xd: 1,2-dichloro-3,3,3-trifluoropropene Example 2

The fluoridation reaction was performed as in Example 1, except that the temperature of the reactor was changed to 330° C. Table 1 shows the results.

Example 3

The fluorination reaction was performed as in Example 1, except that the flow rates of hydrogen fluoride gas, HCFO-1233xf, and chlorine gas were changed to 179 Nml/min, 3.89 Nml/min, and 0.0389 Nml/min, respectively. Table 1 shows the results.

Comparative Example 1

The fluorination reaction was performed as in Example 1, except that oxygen gas was supplied to the reactor at a flow rate of 0.797 Nml/min, in place of chlorine gas. Table 2 shows the results.

Comparative Example 2

The fluorination reaction was performed as in Example 1, except that oxygen gas was supplied to the reactor at a flow rate of 0.0797 Nml/min, in place of chlorine gas. Table 2 shows the results.

Comparative Example 3

The fluorination reaction was performed as in Example 1, except that the flow rate of chlorine gas was changed to 0.195 Nml/min. Table 2 shows the results.

Comparative Example 4

The fluorination reaction was performed as in Example 1, except that oxygen gas was supplied to the reactor at a flow rate of 2.00 Nml/min, in place of chlorine gas, the temperature of the reactor was changed to 300° C., and the flow rates of hydrogen fluoride gas and HCFO-1233xf were changed to 280 Nml/min and 20.0 Nml/min, respectively. Table 2 shows the results.

Comparative Example 5

The fluorination reaction was performed as in Example 1, except that oxygen gas was supplied to the reactor at a flow rate of 0.797 Nml/min, in place of chlorine gas, and the temperature of the reactor was changed to 330° C. Table 2 shows the results.

TABLE 1

|  | Examples | | |
| --- | --- | --- | --- |
|  | 1 | 2 | 3 |
| Reaction temperature (° C.) | 350 | 330 | 350 |
| Contact time (W/F$_0$/Nml · sec) | 1.7 | 1.7 | 2.3 |
| Hydrogen fluoride:Starting material (Molar ratio) | 30:1 | 30:1 | 46:1 |
| Catalyst deterioration inhibitor | | | |
| Type | | Chlorine | |
| Mol % based on starting material | 1% | 1% | 1% |
| 1233xf conversion (GC %) | 7.1 | 4.7 | 7.5 |
| Selectivity   1234yf | 63.4 | 49.3 | 62.3 |
| (GC %)        245cb | 20.4 | 24.4 | 21.6 |
|               1223xd | 2.9 | 6.8 | 2.3 |
|               Others | 13.3 | 19.5 | 13.8 |
|          1234yf + 245cb | 83.8 | 73.7 | 83.9 |
| Speed of reduction in conversion (GC %/hr) | 0.0 | 0.0 | 0.0 |

TABLE 2

|  | Comparative Examples | | | | |
| --- | --- | --- | --- | --- | --- |
|  | 1 | 2 | 3 | 4 | 5 |
| Reaction temperature (° C.) | 350 | 350 | 350 | 300 | 330 |
| Contact time (W/F$_0$/Nml · sec) | 1.7 | 1.7 | 1.7 | 1.7 | 1.7 |
| Hydrogen fluoride:Starting material (Molar ratio) | 30:1 | 30:1 | 30:1 | 14:1 | 30:1 |
| Catalyst deterioration inhibitor | | | | | |
| Type | Oxygen | Oxygen | Oxygen | Oxygen | Oxygen |
| Mol % based on starting material | 10% | 1% | 5% | 10% | 10% |
| 1233xf conversion (GC %) | 5.4 | 1.9 | 7.4 | 1.7 | 2.9 |
| Selectivity   1234yf | 63.5 | 66.0 | 55.4 | 39.0 | 50.8 |
| (GC %)        245cb | 19.3 | 20.0 | 16.8 | 25.8 | 25.2 |
|               1223xd | 0.0 | 0.0 | 14.5 | 0.0 | 0.0 |
|               Others | 17.2 | 14.0 | 13.3 | 35.2 | 24.0 |
|          1234yf + 245cb | 82.8 | 86.0 | 72.2 | 64.8 | 76.0 |
| Speed of reduction in conversion (GC %/hr) | 0.5 | 1.0 | 0.0 | 0.3 | 0.3 |

As is clear from the above results, when chlorine gas was used as a catalyst deterioration inhibitor (Examples 1 to 3), 2,3,3,3-tetrafluoropropene (HFO-1234yf), which is a target product, and 1,1,1,2,2-pentafluoropropane (HFC-245cb), which is a useful compound, were obtained with high selectivity, although chlorine gas was used in an amount as small as 1 mol % based on the starting material, and the reaction temperature was as low, relatively, as 330 to 350° C. Further, a decrease in the starting material conversion was not observed with time, which indicates that catalyst deterioration was prevented.

In contrast, when oxygen was used as a catalyst deterioration inhibitor, and the reaction temperature was lowered, the starting material conversion was greatly reduced, and the effect of preventing reduction in conversion with time was insufficient although oxygen was used in an amount as large as 10 mol % based on the starting material (Comparative Examples 1, 4, and 5). In particular, when the oxygen amount was 1 mol % based on the starting material (Comparative Example 2), the starting material conversion was low, and the effect of preventing reduction in conversion with time was insufficient although the reaction temperature was 350° C. Further, when chlorine gas was used as a catalyst deterioration inhibitor in an amount of 5 mol % based on the starting material (Comparative Example 3), the selectivity of 2,3,3,3-tetrafluoropropene (HFO-1234yf), which was the target product, was decreased while HCFO-1223xd, which was a chlorinated product, was formed in a large amount as a by-product.

The invention claimed is:

1. A method for producing a fluorine-containing olefin of Formula (7): $CF_3CA$=$CHB$, wherein one of A or B is F, and the other is H,
    the method comprising reacting anhydrous hydrogen fluoride with at least one chlorine-containing compound in the presence of a chromium atom-containing fluorination catalyst, the at least one chlorine-containing compound being selected from the group consisting of
    a chlorine-containing alkane of Formula (1): $CX_3CClYCH_2Z$, wherein X is independently F or Cl, Y is H or F, when Y is H, Z is Cl or F, and when Y is F, Z is H;
    a chlorine-containing alkane of Formula (2): $CX_3CH_2CHX_2$, wherein X is independently F or Cl, and at least one X is Cl;
    a chlorine-containing alkene of Formula (3): $CX_3CCl$=$CH_2$, wherein X is independently F or Cl;
    a chlorine-containing alkene of Formula (4): $CX_3CH$=$CHX$, wherein X is independently F or Cl, and at least one X is Cl;
    a chlorine-containing alkene of Formula (5): $CH_2XCCl$=$CX_2$, wherein X is independently F or Cl; and
    a chlorine-containing alkene of Formula (6): $CHX_2CH$=$CX_2$, wherein X is independently F or Cl, and at least one X is Cl;
    the reaction being carried out at a temperature within a range of 200 to 350° C. in the presence of 0.0001 to 0.03 mol of molecular chlorine per mol of the chlorine-containing compound.

2. The method for producing a fluorine-containing olefin according to claim 1, wherein the chlorine-containing compound is at least one compound selected from the group consisting of 2,3-dichloro-1,1,1-trifluoropropane, 1,2,3-trichloro-1,1-difluoropropane, 1,1,2,3-tetrachloro-1-fluoropropane, 1,1,1,3,3-pentachloropropane, 2-chloro-3,3,3-trifluoropropene, 2,3,3,3-tetrachloropropene, 2,3-dichloro-3,3-difluoropropene, 1-chloro-3,3,3-trifluoropropene, 1,3,3,3-tetrachloropropene, 1,1,2,3-tetrachloropropene, and 1,1,3,3-tetrachloropropene.

3. The method for producing a fluorine-containing olefin according to claim 1, wherein the chlorine-containing compound is 2-chloro-3,3,3-trifluoropropene, and the reaction temperature is 300 to 350° C.

4. The method for producing a fluorine-containing olefin according to claim 1, wherein the molecular chlorine is used in an amount of 0.001 to 0.01 mol per mol of the chlorine-containing compound.

5. The method for producing a fluorine-containing olefin according to claim 2, wherein the chlorine-containing compound is 2-chloro-3,3,3-trifluoropropene, and the reaction temperature is 300 to 350° C.

6. The method for producing a fluorine-containing olefin according to claim 2, wherein the molecular chlorine is used in an amount of 0.001 to 0.01 mol per mol of the chlorine-containing compound.

7. The method for producing a fluorine-containing olefin according to claim 3, wherein the molecular chlorine is used in an amount of 0.001 to 0.01 mol per mol of the chlorine-containing compound.

* * * * *